United States Patent [19]

Abe et al.

[11] Patent Number: 5,117,055

[45] Date of Patent: May 26, 1992

[54] METHOD FOR DIRECT CONVERSION OF FLUOROCARBONYL GROUP INTO HALOGENIDES

[75] Inventors: Takashi Abe, Kasugai; Eiji Hayashi, Konan; Haruhiko Fukaya, Oobu, all of Japan

[73] Assignees: Agency of Industrial Science & Technology; Ministry of International Trade & Industry, both of Tokyo, Japan

[21] Appl. No.: 482,969

[22] Filed: Feb. 22, 1990

[30] Foreign Application Priority Data

| Mar. 31, 1989 | [JP] | Japan | 1-82726 |
| Mar. 31, 1989 | [JP] | Japan | 1-82727 |
| Mar. 31, 1989 | [JP] | Japan | 1-82728 |
| Mar. 31, 1989 | [JP] | Japan | 1-82729 |

[51] Int. Cl.$^5$ ............ C07C 51/04; C07C 51/363; C07C 51/377; C07C 41/22; C07C 209/68; C07C 209/78; C07D 207/00; C07D 265/30

[52] U.S. Cl. ............ 562/849; 562/824; 562/825; 562/844; 562/845; 562/850; 544/98; 546/184; 546/248; 548/566; 548/567; 548/570; 548/571; 548/579; 564/1; 564/461; 564/462; 564/463; 564/510; 564/511; 568/74; 568/75; 568/77; 568/589; 568/583; 568/584; 568/587; 568/669; 568/611; 570/170

[58] Field of Search ............ 562/856, 864, 824, 825, 562/844, 849, 850; 570/172, 163, 131, 132, 134, 133, 170; 568/849, 31, 589, 683, 684, 74, 75, 77, 589, 583, 584, 587, 669, 671; 544/98; 548/570, 571, 579, 556, 557; 546/184, 248; 564/1, 461, 462, 463, 510, 511

[56] References Cited

U.S. PATENT DOCUMENTS

| 2,647,933 | 8/1953 | La Zerte et al. | |
| 2,704,776 | 3/1955 | La Zerte et al. | |
| 3,456,024 | 7/1969 | Loree | |
| 3,535,393 | 10/1970 | Bloechl | 570/172 |
| 4,379,768 | 4/1983 | Yamabe et al. | 562/850 |

FOREIGN PATENT DOCUMENTS 1218528  1/1971  United Kingdom .

OTHER PUBLICATIONS

Journal of Chemical Society, pp. 584-587, 1951, R. N. Haszeldine, "The Reactions of Metallic Salts of Acids with Halogens. Part I. The Reaction of Metal Trifluoroacetates with Iodine, Bromine, and Chlorine".
Journal of Organic Chemistry, vol. 23, 1958, pp. 2016-2017, C. G. Krespan, "Preparation of Fluoroalkyl Iodides from Fluorinated Acid Chlorides".
Journal of Organic Chemistry, vol. 32, Mar. 1967, pp. 833-834, D. Paskovich et al., "Simplified Method for the Preparation of Fluoroalkyl Iodides".
Asashi Glass Research Report, vol. 32, 1982, pp. 117-129, M. Kato et al., "A New Synthetic Method of Perfluoroalkanephosphonates and Related Compound Preparation".
Journal of Chemical Society, 1961, pp. 3779-3787, R. D. Chambers et al., "Mixtures of Halogens and Halogen Polyfluorides as Effective Sources of the Halogen Monofluorides in Reactions with Fluoro-Olefins".
Journal of Organic Chemistry, vol. 27, May, 1962, pp. 1813-1814, C. G. Krespan, "Synthesis of Fluoroalkyl Iodides".
Journal of Organometallic Chemistry, vol. 57, 1973, pp. 423-433, B. L. Dyatkin et al., "On the Interaction of Perfluoroalkyl Carbanions with Silver Salts".
Journal of American Chemical Society, vol. 73, pp. 4016-4017, T. J. Brice et al., "Fluorocarbon Chemistry. IV. The Preparation and Some Reactions of Silver Undecafluorocyclohexanecarboxylate", 1951.
Journal of American Chemical Society, vol. 74, 1952, pp. 848-851, M. Hauptschein et al., "Perfluoroalkyl Halides Prepared from Silver Perfluoro-Fatty Acid Salts. III. 1,3-Dibromohexafluoropropane and 1,3-Dichlorohexafluoropropane".
Brace, "Some Approaches to the Synthesis of Fluorinated Alcohols and Esters. I. Completely Fluorinated Esters from Hunsdiecker Reaction of Silver F-Alkanoates with Iodine", Journal of Fluorine Chemistry, vol. 18, (1981), pp. 515-524.

*Primary Examiner*—Marianne Cintins
*Assistant Examiner*—Margaret J. Argo
*Attorney, Agent, or Firm*—Oblon, Spivak, McClelland, Maier & Neustadt

[57] ABSTRACT

A perfluoroalkyl halogenide represented by the formula:

$$R_f \diagdown \begin{matrix} (X)_n \\ (CF)_{n-m} \\ \| \\ O \end{matrix}$$

wherein X stands for one element selected from the group consisting of iodine and bromine, $R_f$ for a perfluorohydrocarbon group, n for an integer in the range of 1 to 3, and m for an integer in the range of 1 to 3, provided that n and m satisfy the relationship, $n \geq m$, is produced by a method which consists essentially in subjecting a perfluorocarboxylic acid fluoride represented by the formula, $$R_f(-C-F)_n \atop \underset{O}{\|}$$

wherein $R_f$ and n have the same meanings as defined above, to a thermal reaction with a lithium halogenide represented by XI, wherein X has the same meaning as defined above.

5 Claims, No Drawings

METHOD FOR DIRECT CONVERSION OF FLUOROCARBONYL GROUP INTO HALOGENIDES

BACKGROUND OF THE INVENTION

1. Field of the Invention

This invention relates to a novel method for the production of perfluoroalkyl halogenides (iodides and bromides). More particularly, this invention relates to a method for economically and advantageously producing perfluoroalkyl halogenides useful as intermediates for the synthesis of fluorine-containing products such as, for example, surfactants, agricultural pesticides, and medicines in high yields from readily available raw materials.

2. Prior Art Statement

In recent years, iodine-containing perfluoro compounds have been attracting attention as intermediates and raw materials for the synthesis of various fluorine-containing products. They have found extensive utility as intermediates for the synthesis of surfactants, agricultural pesticides, and medicines, for example. Bromine-containing perfluoro compounds have found extensive utility for the synthesis of similar products and as Halon type anti-inflammatory agents and X-ray shielding agents.

The conventional methods for the production of perfluoroalkyl iodides may be broadly divided into those of the type using perfluorocarboxylic acid derivatives as raw materials and those of the type using fluorine-containing olefins as raw materials. The methods of the former type include a method which comprises heating the silver salt of a perfluorocarboxylic acid and iodine ["Journal of Chemical Society", page 584 (1951)], a method which comprises causing a perfluoroalkanoyl chloride to react with potassium iodide ["Journal of Organic Chemistry", Vol. 23, page 2016 (1958)], a method which comprises causing an alkali metal salt of a perfluorocarboxylic acid to react with iodine in a polar solvent ["Journal of Organic Chemistry", Vol. 32, page 833 (1967)] or in a nonpolar solvent (Japanese Patent Public Disclosure SHO 63(1988)-159336), and a method which comprises causing a perfluorocarboxylic acid to react with iodine in the presence of a peroxide ["Asahi Glass Research Report", Vol. 32, page 117 (1982)], for example.

The methods of the latter type include a method which comprises subjecting a mixture of a fluorine-containing olefin with iodine and iodinepentafluoride to thermal reaction ["Journal of Chemical Society", page 3779 (1961)], a method which comprises causing a fluorine-containing olefin to react with iodine in the presence of potassium fluoride as a catalyst in a polar solvent ["Journal of Organic Chemistry", Vol. 27, page 1813 (1962)], and a method which comprises causing a fluorine-containing olefin to react with iodine in the presence of silver fluoride as a catalyst in a polar solvent ["Journal of Organometallic Chemistry", Vol. 57, page 423 (1973)], for example.

While the methods of the latter type using perfluoroolefins (having at least three carbon atoms) necessarily produce secondary or tertiary perfluoroalkyl iodides, the methods of the former type have an advantage in that desired perfluoroalkyl iodides can be produced by using corresponding perfluorocarboxylic acids as raw materials. The conventional methods using perfluorocarboxylic acids as raw materials, however, entail a disadvantage in that they are highly inconvenient for commercial operation because they necessitate use of a dangerous peroxide or conversion of a perfluorocarboxylic acid into an acid chloride or a metallic salt in preparation for the actual reaction.

The methods heretofore known for the production of perfluoroalkyl bromides include those using perfluorocarboxylic acids as raw materials, e.g. a method which comprises heating a silver salt of a perfluorocarboxylic acid and bromine in a sealed tube ["Journal of American Chemical Society", Vol. 73, page 4016 (1951) and Vol. 74, pages 848–849 (1952)] and a method which comprises causing a perfluorocarboxylic anhydride to react with bromine in a carbon-lined tube filled with activated carbon (U.S. Pat. Nos. 2,647,933; 2,704,776).

The methods using perfluorocarboxylic acids as raw materials, however, have a disadvantage in that they are highly inconvenient for commercial operation because they necessitate a complicated step of converting a perfluorocarboxylic acid into a metal salt or an acid anhydride in preparation for the reaction.

Still other methods heretofore proposed include a method which comprises causing perfluoroalkylsulfur pentafluoride to react with bromine at an elevated temperature of about 500° C. in an alumina tube containing nickel chips (U.S. Pat. No. 3,456,024) and a method which comprises causing perfluoroalkyl iodide to react with bromine in the presence of a peroxide (Japanese Patent Public Disclosure SHO 60(1985)-184033 and SHO 61(1986)-233637), for example.

Perfluorocarboxylic acid fluorides are easily produced by electrolytic fluorination of carboxylic acid chloride or oligomerization of perfluoropropene oxide and tetrafluoroethylene oxide, for example. When perfluorocarboxylic acid fluorides are used as raw materials for the production of perfluoroalkyl halogenides via fluorine-containing carboxylic acid derivatives, this production can be performed by a simplified process and accordingly proves to be highly advantageous.

SUMMARY OF THE INVENTION

This invention aims to provide a method for producing perfluoroalkyl halogenides useful as intermediates for the synthesis of various fluorine-containing compounds from readily available perfluorocarboxylic acid fluorides by a simple procedure in high yields.

The present inventors continued a study for accomplishing the object described above. They consequently found that, by subjecting a perfluorocarboxylic acid fluoride to thermal reaction with a lithium halogenide (LiI or LiBr), corresponding perfluoroalkyl halogenides are obtained in high yields. The present invention has been completed based on this knowledge.

To be specific, the present invention is directed to a method for the production of a perfluoroalkyl halogenide represented by the formula,

(II)

wherein X stands for one element selected from the group consisting of iodine and bromine, $R_f$ for a perfluorohydrocarbon group, m for an integer in the range of 1 to 3, n for an integer in the range of 1 to 3, and n ≧m, which method consists essentially in subjecting a perfluorocarboxylic acid fluoride represented by the formula,

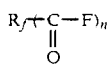 (I)

wherein $R_f$ and n have the same meanings as defined above, to thermal reaction with a lithium halogenide represented by the formula, LiX, wherein X has the same meaning as defined above.

DETAILED DESCRIPTION OF THE PREFERRED EMBODIMENTS

In the method of the present invention, perfluorocarboxylic acid fluorides represented by general formula (I) mentioned above are used as raw materials. In the general formula (I), $R_f$ stand s for a perfluorohydrocarbon group, namely a hydrocarbon group having all hydrogen atoms thereof substituted each with a fluorine atom. Preferably, this group has 1 to 15 carbon atoms. This group may contain a chlorine atom, a bromine atom, an oxygen atom, a nitrogen atom, or a hexavalent sulfur ($-SF_4-$, $-SF_5-$, or $-SO_2F$), for example, as a hetero atom. The perfluorohydrocarbon group may be in linear, branched, or cyclic form. It may be a heterocyclic group containing an oxygen atom, a sulfur atom, or a nitrogen atom as a hetero atom.

Specifically, the perfluorocarboxylic acid fluorides which answer the description given above include trifluoroacetyl fluoride, perfluoropropionyl fluoride, perfluoro-n-butyryl fluoride, perfluoro-n-caproyl fluoride, perfluoro-n-capryl fluoride, perfluoro-2-propoxypropionyl fluoride, 2-bis(trifluoromethyl)propionyl fluoride, perfluoro(2-(n-propoxy)propionyl fluoride), perfluoro (3-(n- propoxy)propionyl fluoride), chlorodifluoroacetyl fluoride, dichlorofluoroacetyl fluoride, bromodifluoroacetyl fluoride, perfluoromalonyl fluoride, perfluorosuccinyl fluoride, perfluoroglutaryl fluoride, perfluorocyclohexylcarbonyl fluoride, perfluoro(1,4-di(fluorocarbonyl)cyclohexane), perfluoro(1,3,5-tri(fluorocarbonyl)cyclohexane), perfluoro(N,N-dimethylaminoacetyl fluoride), perfluoro(3-dimethylamino-propionyl fluoride), perfluoro(3-diethylamino-isobutyl fluoride), perfluoro(3-diethylaminopropionyl fluoride), perfluoro(3-pyrrolidinopropionyl fluoride), perfluoro(2-(methylpyrrolidino)propionyl fluoride), perfluoro(2-morpholinopropionyl fluoride), perfluoro(3-morpholinopropionyl fluoride), perfluoro(3-morpholino-iso-butyryl fluoride), perfluoro(2-piperidinopropionyl fluoride), perfluoro(3-piperidinopropionyl fluoride), perfluoro(3-fluorosulfonylpropionyl fluoride), perfluoro(2-fluorosulfonylpropionyl fluoride), and 3-(pentafluoro-6-sulfonyl)-tetrafluoropropionyl fluoride, for example.

Among the perfluorocarboxylic acid fluorides mentioned above, trifluoroacetyl fluoride, perfluoro(2-propoxypropionyl fluoride), 2-bis(trifluoromethyl)propionyl fluoride, perfluoroglutaryl fluoride, perfluoro(N,N-dimethylaminoacetyl fluoride), perfluoro(2-(piperidino)propionyl fluoride), perfluoro(2-(methylpyrrolidino)propionyl fluoride), perfluoro(3-fluorosulfonylpropionyl fluoride), perfluoro(3-(n-propoxy)propionyl fluoride), perfluoro(3-dimethylamino)propionyl fluoride), and perfluoro(3-pyrrolidinopropionyl fluoride) prove to be particularly desirable.

The lithium halogenide, LiX (X for I or Br), which is the other raw material for the method of this invention may be an anhydride or a hydrate. From the standpoint of yield and purity of the particular perfluoroalkyl halogenide to be obtained, the anhydride is more desirable than the hydrate.

The amount of the lithium halogenide to be used is desired to be slight in excess stoichiometrically relative to the fluorocarbonyl group present in the molecular unit. This amount is advantageously selected in the range of 1.2 to 1.5 mols in the case of a monobasic acid fluoride, 2.5 to 3.0 mols in the case of a dibasic acid fluoride, or 3.5 to 4.0 mols in the case of a tribasic acid fluoride, each per mol of the perfluorocarboxylic acid fluoride.

When a dibasic or tribasic perfluorocarboxylic acid fluoride is used as the raw material, only part of the fluorocarbonyl group can be converted into a halogen (iodine or bromide) by selecting the molar ratio between the perfluorocarboxylic acid fluoride and the lithium halogenide, LiX (X for I or Br), as raw materials.

As shown by the following formula, for example, not only perfluoro (ω,ω'-diiodoalkane) (V) but perfluoro(ω-iodoalkanoyl iodoalkanoyl fluoride) (IV) can be produced from a bifunctional perfluorocarboxylic acid fluoride (III).

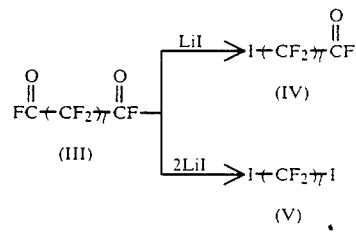

When the conversion by the method of this invention is effected to produce an iodine compound by the use of LiI, the reaction temperature is generally selected in the range of 150° C. to 400° C., preferably in the range of 180° C. to 230° C. A reaction temperature of less than 150° C. is not practical because the reaction at such a temperature has an unduly low conversion. Conversely, a reaction temperature exceeding 400° C. is undesirable because the reaction at such a temperature entails such secondary reaction as decomposition.

When the conversion by the method of this invention is carried out to produce a bromine compound by the use of LiBr, the reaction temperature is selected generally in the range of 300° C. to 500° C., preferably in the range of 320° C. to 400° C. A reaction temperature of less than 300° C. is not practical because the reaction at such a temperature has an unduly low conversion. Conversely, a reaction temperature exceeding 500° C. is undesirable because the reaction at such a temperature tends to entail such secondary reactions as decomposition.

In this reaction for the conversion, the reaction time cannot be unconditionally fixed because it varies with the reaction temperature. Generally, it falls in the range of 5 seconds to 24 hours.

Further, the reaction may be carried out under a vacuum, atmospheric pressure, or an increased pressure. It can be carried out batchwise or continuously, whichever suits the occasion. In this reaction, an inert gas such as nitrogen, helium or argon, or an inert liquid such as perfluorocarbon which avoids reacting with lithium bromide may be used as a diluent, depending on the particular form of the reaction involved. In this case, the ratio of dilution is not desired to exceed 100 times the original volume.

When the reaction is to be carried out continuously, a perfluoroalkyl iodide or a perfluoroalkyl bromide can be easily obtained by continuously supplying a corresponding perfluorocarboxylic acid fluoride as a raw material to a bed packed with a lithium halogenide, LiX (X for I or Br), and kept at a stated temperature. The material of which the reactor is made is not particularly critical. Generally, the reactor used for the reaction is made of stainless steel or Hastelloy. The form of the packed bed is not particularly critical. The packed bed may be a fixed bed, a moving bed, or a fluidized bed, whichever best suits the occasion.

In accordance with the method of this invention, a perfluoroalkyl iodide or a perfluoroalkyl bromide can be obtained in a high yield by using a corresponding fluorine-containing carboxylic acid fluoride which is readily available and subjecting this fluoride to a thermal reaction with a lithium halogenide, LiX (X for I or Br). The product of this reaction is useful as an intermediate for the synthesis of such fluorine-containing products as surfactants, agricultural pesticides, and medicines and as an X-ray contrast medium (in the case of a bromide).

For more specific illustration of the present invention, the following examples are presented which are intended to be merely illustrative of, and not in any sense limitative of, the invention.

EXAMPLE 1

A thick-wall ampoule (14 mm in inside diameter and 170 mm in length) of Pyrex containing 1.36 g of anhydrous lithium iodide was condensed with 17.2 ml (0.77 mmol) of trifluoroacetyl fluoride measured out by means of PVA technique. The ampoule was held in an electric furnace at 180° C. for 7 hours to effect reaction of the contents of the ampoule.

After the reaction was completed, the product was refined by fractional condensation using a trap kept cooled with liquefied nitrogen ($-196°$ C.) and a dry ice-ethanol bath ($-78°$ C.). Consequently, 15.7 ml of a gas (1 atmosphere) was obtained from the cooling trap at $-196°$ C. By $^{19}$F-NMR and IR analysis, this gas was identified to be a mixture of trifluoromethyl iodide and trifluoroacetyl iodide (80:20 by weight ratio).

EXAMPLE 2

A reaction was carried out by substantially following the procedure of Example 1, except that perfluoro(2-(n-propoxy)propionyl fluoride) which was liquid at normal room temperature was used as a perfluorocarboxylic acid fluoride. Specifically, a Pyrex ampoule containing 0.98 g of anhydrous lithium iodide was charged with 1.80 g (5.42 mmols) of perfluoro(2-(n-propoxy)-propionyl fluoride). The reaction mixture thus prepared in the ampoule was left reacting at 180° C. for 6.5 hours.

After the reaction was completed, the ampoule was opened and cooled with liquefied nitrogen to expel the volatile gas (mainly carbon monoxide). Then, the ampoule was warmed to room temperature and the reaction product was transferred out via a vacuum line and weighed. Thus, 1.90 g of a transparent purple liquid was obtained. When this liquid was analyzed by gas chromatography [carrier gas: He, liquid phase: 1,6-bis(1,1,12-trihydroperfluorododecyloxy)hexane, carrier: 60- to 80-mesh Chromosorb PAW], IR, $^{19}$F-NMR, and Mass, there was obtained 1.77 g of perfluoro(1-(n-propoxy)-1-iodoethane). The yield was 79 mol % based on the raw material.

This compound possessed a boiling point of 84.0° C. to 85.0° C., $n_D^{20}$ of 1.3153, and $d_4^{20}$ of 1.9859 and assumed the state of purple liquid at room temperature.

EXAMPLE 3

A reaction was carried out by following the procedure of Example 2, except that 2,2-bis(trifluoromethyl)-propionyl fluoride was used as the raw material.

Specifically, when 2.03 g of 2,2-bis(trifluoromethyl)-propionyl fluoride was caused to react with 1.60 g of anhydrous lithium iodide at 180° C. for 7 hours, there was obtained 1.92 g of a reddish purple liquid solidified at room temperature. When this product was analyzed in the same manner as in Example 2, there was obtained 1.43 g of 1,1-bis(trifluoromethyl)-iodoethane. A small amount of 2,2-bis(trifluoromethyl)ethane was by-produced. The yield of 1,1-bis(trifluoromethyl)-iodoethane was 78 mol % based on the raw material consumed.

This compound has never been reported before. At room temperature, it was a light purple sublimable solid substance.

The spectroscopic data (NMR and Mass data) of this compound are shown below.

NMR Data

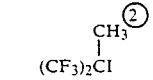

$^{19}$F-NMR (CFCl$_3$ basis)
① $-70.6$ ppm
$^1$H-NMR (TMS basis)
② 2.19 ppm

Mass analysis data m/e
292 M$^+$
273 [M—F]$^+$
202 C$_3$F$_2$HI$^-$

EXAMPLE 4

A reaction was carried out by following the procedure of Example 3, except that perfluoroglutaryl fluoride, a dibasic acid, was used as a fluorine-containing carboxylic acid fluoride and a reactor of stainless steel having an inner volume of 75 ml was used as a reaction vessel.

Specifically, when 1.50 g (6.15 mmol) of perfluoroglutaryl fluoride was caused to react with 0.78 g (5.83 mmols) of anhydrous lithium iodide at 180° C. for 7 hours, there was obtained 1.80 g of a transparent purple liquid. When this liquid was analyzed in the same manner as in Example 3 [gas chromatography: carrier gas: He, liquid phase: KeLF #90, carrier: 60 to 80-mesh Chromosorb PAW], there were obtained 0.70 g of perfluoro(4-iodobutyryl fluoride) and 0.37 g of perfluoro(1,3-diiodopropane). Their yields were 50 mol % and 21 mol % respectively, based on the raw materials consumed. The physicochemical properties of the methyl ester of perfluoro(3-iodo-butyric acid) were a boiling point of 159.5° C. to 160.5° C., $n_D^{20}$ of 1.3902, and $d_4^{20}$ of 1.9460. In the infrared absorption spectrum of this compound, the characteristic absorption due to

was present at $\nu(C=O)$ j1,784 cm$^{-1}$.

EXAMPLE 5

A reaction was carried out by following the procedure of Example 4, except that the molar ratio between perfluoroglutaryl fluoride and anhydrous lithium iodide was substantially 1:2.

Specifically, when a reaction mixture consisting of 1.50 g (6.15 mmols) of perfluoroglutaryl fluoride and 1.68 g (12.56 mmols) of anhydrous lithium iodide was left reacting at 180° C. for 7 hours, there was obtained 2.03 g of a transparent purple liquid. When this liquid was analyzed in the same manner as in Example 4, there was obtained 1.78 g of perfluoro(1,3-diiodopropane). The yield of this compound was 72 mol % based on the raw material supplied. This compound was a transparent light purple liquid at room temperature and possessed physicochemical properties of a boiling point of 130.0° C. to 131.0° C., $n_D^{20}$ of 1.4517, and 0 of 2.5795.

EXAMPLE 6

The product obtained by electrolytically fluorinating methyl N,N-dimethylaminoacetate was used as a raw material. This product contained 62.5% by weight of perfluoro(N,N-dimethylaminoacetyl fluoride).

First, a reactor of stainless steel having an inner volume of 75 ml and containing 4.64 g of anhydrous lithium iodide was charged with 9.39 g of the aforementioned fluorocarbon mixture (containing 5.87 g of perfluoro-(N,N-dimethylaminoacetyl fluoride) and then deaerated. The reactor was heated at 180° C. for 7 hours to effect reaction of the reaction mixture held therein. The reaction product was divided into two fractions by fractionating condensation using cooling traps kept at −195° C. and −78° C. When the compound condensed at −78° C. cold trap was analyzed in the same manner as in Example 2, there was obtained 4.54 g of perfluoro(N,N-dimethylamino)methyl iodide). The yield of this compound was 74 mol % based on the raw material consumed.

The perfluoro((N,N-dimethylamino)methyl iodide) was a novel compound, exhibited a boiling point of 56.5° C. to 57.0° C., $n_D^{20}$ of 1.3310, and $d_4^{20}$ of 2.0685, and assumed the state of a light purple liquid at room temperature.

The spectroscopic data of this compound were as shown below.

| $^{19}$F-NMR data | |
|---|---|
| (CF$_3$)$_2$N ① | CF$_2$I ② |
| Chemical shift (ppm: CFCl$_3$ basis) | |
| ① | −54.6 (triplet) |
| ② | −19.8 (heptet) |
| Coupling constant (Hz) | |
| ①−② = 13.4 | |
| Mass analysis data | |
| m/e | |
| 310 | [M−F]$^+$ |
| 222 | C$_2$F$_3$NI$^+$ |
| 202 | (CF$_3$)$_2$NCF$_2$$^-$ |

EXAMPLE 7

A reaction was carried out by following the procedure of Example 6, except that the product obtained by electrolytically fluorinating methyl 2-piperidinopropionate was used as a raw material.

When 5.03 g of a fluorocarbon mixture (containing 3.47 g of perfluoro(2-(piperidino)propionyl fluoride) and 0.68 g of perfluoro(2-(methylpyrrolidino)propionyl fluoride) was caused to react with 1.69 g of anhydrous lithium iodide at 180° C. for about 6 hours and the resultant reaction product was analyzed in the same manner as in Example 6, the product was found to contain 2.10 g of perfluoro[1-(piperidino)ethyl iodide] and 0.63 g of perfluoro[1-(methylpyrrolidino)ethyl iodide].

The yields of perfluoro(1-(piperidino)ethyl iodide) and perfluoro(1-(methylpyrrolidino)ethyl iodide) were 51 mol % and 78 mol % respectively, based on the raw materials.

The perfluoro(1-(piperidino)ethyl iodide) was a novel compound. The physicochemical properties of this compound were a boiling point of 140.0° C. to 140.5° C., $n_D^{20}$ of 1.3527, and $d_4^{20}$ of 2.1313. The maximum ultraviolet absorption, $\lambda_{max}$, was 293 nm. This value compares favorably with that of perfluoro(t-butyl iodide), now attracting attention as the material for the iodine-solar-pumped laser, ($\lambda_{max}$=290±0.8; B. M. Tabibi, M. H. Lee, J. H. Lee and W. R. Weaver, Proc. Int. Conf. Lasers, 1986, 144).

EXAMPLE 8

The product obtained by electrolytically fluorinating sultone was used as a raw material. This product obtained 50.9% of perfluoro(3-fluorosulfonylpropionyl fluoride).

A reactor of stainless steel having an inner volume of 30 ml and containing 1.87 g of anhydrous lithium iodide was charged with 4.15 g of the fluorocarbon mixture (containing 2.11 g of perfluoro(3-fluorosulfonylpropionyl fluoride)) and then deaerated. The reactor was heated at 180° C. for about 5 hours to effect reaction of the reaction mixture. When the reaction product was analyzed in the same manner as in Example 6, there was obtained 1.5 g of perfluoro(2-iodo-ethanesulfonyl fluoride). The yield of this product was 69.6% based on the raw material consumed.

The perfluoro(2-iodo-ethanesulfonyl fluoride) was a novel compound, possessed a boiling point of 94.5° C. to 95.5° C., $n_D^{20}$ of 1.3902, and $d_4^{20}$ of 2.2167, and assumed the state of a light purple liquid at room temperature.

The spectroscopic data (NMR and IR) of this compound were as shown below.

| NMR data | | |
|---|---|---|
| ① | ② | ③ |
| ICF$_2$− | CF$_2$− | SO$_2$F |
| Chemical shift (ppm: CFCl$_3$ basis) | | |
| ① | | −60.4 (t-d) |
| ② | | −101.3 (d-t) |
| ③ | | 48.8 (t-t) |
| (t: triplet, d: doublet) | | |
| Coupling constant (Hz) | | |
| ① − ② = 6.8 | | |
| ② − ③ = 7.7 | | |

-continued

① − ③ = 6.4

IR data 1,467 cm$^{-1}$: asym $\nu(SO_2)$

EXAMPLE 9

A thick-wall ampoule of Pyrex (14 mm in inside diameter and 170 mm in height) containing 0.60 g of lithium bromide was charged with 1.48 mmols of perfluoro(3-(n-propoxy)propionyl fluoride). The reaction mixture thus prepared was left reacting at 350° C. for 4 hours. After the reaction was completed, the ampoule was cooled with liquefied nitrogen to expel the volatile gas (mainly carbon monoxide). Then the contents of the ampoule were warmed to room temperature, transferred out through a vacuum line, and weighed. Consequently, there was obtained 1.53 g of a transparent light orange liquid.

When this liquid was analyzed in the same manner as in Example 4, there was obtained 1.41 g of perfluoro(2-bromoethyl-n-propyl ether). The yield of the product was 87 mol % based on the raw material supplied.

This compound was a transparent liquid at room temperature. The physicochemical properties of this compound were a boiling point of 68.5° C. to 69.5° C., $n_D^{20}$ of 1.2823, and $d_4^{20}$ of 1.8066.

EXAMPLE 10

A reaction was carried out by following the procedure of Example 3, except that perfluoroglutaryl fluoride, a dibasic acid, was used as a fluorine-containing carboxylic acid fluoride and a reactor of stainless steel having an inner volume of 75 ml was used as a reaction vessel.

Specifically, when 2.03 g (8.32 mmols) of perfluoroglutaryl fluoride was caused to react with 0.70 g (8.20 mmols) of anhydrous lithium bromide at 350° C. for 5.5 hours, there was obtained 2.09 g of a transparent reddish purple liquid which fumed when coming in contact with the air. When this liquid was analyzed in the same manner as in Example 4, there were obtained 0.78 g of perfluoro(4-bromobutyryl fluoride) and 0.43 g of perfluoro(1,3-dibromopropane). The yields of these compounds were respectively 45 mol % and 21 mol %, based on the raw material consumed.

The physicochemical properties of perfluoro(3-bromobutyryl fluoride) as a methyl ester were a boiling point of 132.5° C. to 133.5° C., $n_D^{20}$ of 1.3536, and $d_4^{20}$ of 1.7690. In the infrared absorption spectrum of this compound, the characteristic absorption due to —COMe
‖
O was present at $\nu(C=O)$ 1.787 cm$^{-1}$.

EXAMPLE 11

A reaction was carried out by following the procedure of Example 10, except that the charging molar ration of perfluoroglutaryl fluoride and anhydrous lithium bromide was 1:2.

Specifically, when a reaction mixture consisting of 1.00 g (4.10 mmols) of perfluoroglutaryl fluoride and 0.76 g (8.75 mmols) of anhydrous lithium bromide was left reacting in a Pyrex ampoule at 350° C. for 5 hours, there was obtained 1.17 g of a transparent reddish purple liquid. When this liquid was analyzed in the same manner as in Example 10, there was obtained 1.00 g of perfluoro(1,3-dibromopropane). The yield of this product was 79 mol % based on the raw material charged.

The compound was transparent liquid at room temperature and exhibited physicochemical properties of a boiling point of 71.5° C. to 72.5° C., $n_D^{20}$ of 1.3582, and $d_4^{20}$ of 2.1334.

EXAMPLE 12

A thick-wall ampoule of Pyrex (14 mm in inside diameter and 170 mm in length) containing 0.83 g of anhydrous lithium bromide was charged with 2.14 g (7.14 mmols) of perfluoro[3-(N,N-dimethylamino)propionyl fluoride] and heated at 350° C. for 7 hours to effect reaction of the reaction mixture held in the ampoule. After the reaction was completed, the ampoule was cooled with liquefied nitrogen to expel the volatile gas (mainly carbon monoxide). Then, the reaction product was transferred out at room temperature via a vacuum line. Consequently, there was obtained 2.04 g of a transparent orange liquid.

When this liquid was analyzed un the same manner as in Example 4, there was obtained 1.78 g (5.36 mmols) of perfluoro(N,N-dimethyl-2-bromoethyl amine). The yield of this compound was 75 mol % based on the raw material charged.

This compound was a transparent liquid at room temperature and exhibited a boiling point of 59.5° C. to 60.5° C., $n_D^{20}$ of 1.2963, and $n_4^{20}$ of 1.8932. The spectroscopic data of this compound were as follows.

$^{19}$F-NMR data (CF$_3$)$_2$NCF$_2$CF$_2$Br
      ①  ②  ③

Chemical shift (ppm: CFCl$_3$ basis)

| | |
|---|---|
| ① | −52.8 (t-t) |
| ③ | −66.4 (hept-t) |
| ② | −91.2 (hept-t) |

Coupling constant (Hz)

① − ③ = 8.68
① − ② = 16.12
② − ③ = 2.48

Mass analysis data

| m/e | |
|---|---|
| 314, 312 | [M−F]$^+$ |
| 252 | [M−Br]$^+$ |
| 202 | (CF$_3$)$_2$NCF$_2^-$ |

EXAMPLE 13

A reaction was carried out by following the procedure of Example 12, except that perfluoro(3-pyrrolidinopropionyl fluoride) was used as a nitrogen-containing perfluorocarboxylic acid fluoride.

Specifically, when 1.76 g (4.88 mmols) of perfluoro(3-pyrrolidinopropionyl fluoride) was caused to react with 0.73 g of anhydrous lithium bromide in a Pyrex ampoule at 350° C. for 5 hours, there was obtained 1.43 g of a transparent orange liquid. When this liquid was analyzed in the same manner as in Example 4, there was obtained 1.09 g of perfluoro(1-pyrrolidino-2-bromoethane). The yield of this product was 57 mol % based on the raw material charged.

This compound was a novel compound never before reported and exhibited physicochemical properties of a boiling point of 104.0° C. to 105.0° C., $n_D^{20}$ of 1.3173, and $d_4^{20}$ of 1.9338.

EXAMPLE 14

A reaction was carried out by following the procedure of Example 12, except that the product obtained by electrolyzing methyl 3-morpholino-iso-butyrate (cell-drain compound) was used in its unmodified form as a raw material and a stainless steel reactor having an inner volume of 75 ml was used as a reaction vessel. The fluorination product used herein contained 68.8 wt % of perfluoro(3-morpholino-iso-butyryl fluoride).

When 2.57 g of the fluorocarbon mixture mentioned above (containing 1.77 g of perfluoro(3-morpholino-isobutyryl fluoride)) was caused to react with 0.48 g of anhydrous lithium bromide in a stainless steel reactor at 350° C. for 5 hours, there was obtained 2.53 g of a transparent orange liquid. When this liquid was analyzed in the same manner as in Example 4, it was found to contain 1.13 g of perfluoro(1-morpholino-2-bromopropane). The yield of this compound was 82 mol % based on the raw material consumed.

This compound was a novel compound never before reported, exhibited physicochemical properties of a boiling point of 133.0° C. to 134.0° C., $n_D^{20}$ of 1.3225, and $d_4^{20}$ of 1.9828, and assumed the state of a transparent liquid at room temperature.

What is claimed is:

1. A method for the production of a perfluorohydrocarbon halogenide of the formula:

$$R_f \begin{matrix} (X)_n \\ (CF)_{n-m} \\ \| \\ O \end{matrix}$$

wherein $R_f$ represents a perfluorohydrocarbon group having 1 to 15 carbon atoms, X represents an element selected from the group consisting of iodine and bromine, n is an integer in the range of 1 to 3 and m is an integer in the range of 1 to 3, provided that m and n satisfy the relationship of $n \geq m$, which method comprises mixing a perfluorohydrocarboyxlic acid fluoride of the formula:

$$R_f(C-F)_n$$
$$\| $$
$$O$$

wherein $R_f$ and n have the same meaning as define above, with LiX, wherein X has the same meaning as defined above, and heating the same to a temperature in the range of 150° to 400° C., where X is iodine, and in the range of 300° to 500° C. where X is bromine.

2. The method according to claim 1, wherein said heating temperature is in the range of 180° to 230° C. where X is iodine, and in the range of 320°to 400° C. where X is bromine.

3. The method according to claim 1, wherein $R_f$ contains at least one member selected from the group consisting of chlorine atom, bromine atom, oxygen atom, nitrogen atom, $-SF_4-$, $-SF_5-$ and $-SO_2F$.

4. The method according to claim 1, wherein said perfluorohydrocarboxylic acid fluoride is selected from the group consisting of trifluoroacetyl fluoride, perfluoropropionyl fluoride, perfluoro-n-butyryl fluoride, perfluoro-n-caproyl fluoride, perfluoro-n-capryl fluoride, perfluoro-2-propoxypropionyl fluoride, 2-bis(trifluoromethyl)perfluoropropionyl fluoride, perfluoro(2-(n-propoxy)propionyl fluoride), perfluoro(3-(n-propoxy)propionyl)fluoride, chlorodifluoroacetyl fluoride, dichlorofluoroacetyl fluoride, bromodifluoroacetyl fluoride, perfluoromalonyl fluoride, perfluorosuccinyl fluoride, perfluoroglutaryl fluoride, perfluorocyclohexylcarbonyl fluoride, perfluoro(1,4-di(fluorocarbonyl)-cyclohexane), perfluoro(1,3,5-tri(fluorocarbonyl)cyclohexane), perfluoro(N,N-dimethylaminoacetyl fluoride), perfluoro(3-dimethylamino-propionyl fluoride), perfluoro(3-diethylamino-isobutyl fluoride, perfluoro(3-diethylaminopropionyl fluoride), perfluoro(3-pyrrolidinopropionyl fluoride), perfluoro(2-(methylpyrrolidino)propionyl fluoride), perfluoro(2-morpholinopropionyl fluoride), perfluoro(3-morpholinopropionyl fluoride), perfluoro(3-morpholino-isobutyryl fluoride), perfluoro(2-piperidinopropionyl fluoride), perfluoro(3-piperidinopropionyl fluoride), perfluoro(3-fluorosulfonylpropionyl fluoride), perfluoro(2-fluorosulfonylpropionyl fluoride, and 3-(pentafluoro-$\lambda^6$-sulfonyl)-tetrafluoropropionyl fluoride.

5. The method according to claim 4, wherein the perfluorocarboxylic acid fluoride is selected from the group consisting of trifluoroacetyl fluoride, perfluoro(2-propoxypropionyl fluoride), 2-bis(trifluoromethyl)perfluoropropionyl fluoride, perfluoroglutaryl fluoride, perfluoro(N,N-dimethylaminoacetyl fluoride), perfluoro(2-piperidino)propionyl fluoride), perfluoro(2-(methylpyrrolidino)propionyl fluoride, perfluoro(3-fluorosulfonylpropionyl fluoride), perfluoro(3-(n-propoxy)propionyl fluoride), perfluoro(3-(dimethylamino)propionyl fluoride) and perfluoro(3-(pyrrolidinopropionyl fluoride.

* * * * *

UNITED STATES PATENT AND TRADEMARK OFFICE
CERTIFICATE OF CORRECTION

PATENT NO. :   5,117,055
DATED      :   May 26, 1992
INVENTOR(S) :  Takashi Abe et al.

It is certified that error appears in the above-identified patent and that said Letters Patent is hereby corrected as shown below:

On the Title page, item [73], Assignee should be,

--Agency of Industrial Science & Technology, Ministry of International Trade & Industry, Tokyo, Japan--.

Signed and Sealed this

Twentieth Day of July, 1993

Attest:

MICHAEL K. KIRK

*Attesting Officer*    Acting Commissioner of Patents and Trademarks